United States Patent
Winslow et al.

(10) Patent No.: US 7,338,496 B1
(45) Date of Patent: Mar. 4, 2008

(54) METHOD AND APPARATUS FOR POSITIONING AN IMPLANT

(75) Inventors: Nathan A Winslow, Warsaw, IN (US); Brian K Berelsman, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 486 days.

(21) Appl. No.: 10/651,793

(22) Filed: Aug. 29, 2003

(51) Int. Cl.
*A61F 5/00* (2006.01)

(52) U.S. Cl. ......................................................... 606/87
(58) Field of Classification Search ................. 606/53, 606/86, 87, 96, 97, 98, 99
See application file for complete search history.

(56) References Cited

U.S. PATENT DOCUMENTS

| | | | |
|---|---|---|---|
| 2,239,088 A | 4/1941 | Ettinger | |
| 3,067,740 A | 12/1962 | Haboush | |
| 3,530,854 A * | 9/1970 | Kearney | 606/67 |
| 4,012,796 A | 3/1977 | Weisman et al. | |
| 4,234,309 A * | 11/1980 | Sellers | 433/225 |
| 4,337,773 A | 7/1982 | Raftopoulos et al. | |
| 4,357,716 A | 11/1982 | Brown | |
| 4,624,673 A | 11/1986 | Meyer | |
| 4,718,916 A | 1/1988 | Morscher | |
| 4,770,660 A | 9/1988 | Averill | |
| 4,834,080 A | 5/1989 | Brown | |
| 4,896,662 A | 1/1990 | Noble | |
| 4,944,759 A * | 7/1990 | Mallory et al. | 623/22.31 |
| 4,994,085 A | 2/1991 | Sawai et al. | |
| 5,047,061 A | 9/1991 | Brown | |
| 5,078,746 A | 1/1992 | Garner | |
| 5,080,680 A | 1/1992 | Mikhail et al. | |
| 5,092,892 A | 3/1992 | Ashby | |
| 5,180,395 A | 1/1993 | Klaue | |
| 5,201,769 A | 4/1993 | Schutzer | |
| 5,246,459 A * | 9/1993 | Elias | 623/20.34 |
| 5,282,865 A | 2/1994 | Dong | |
| 5,340,362 A | 8/1994 | Carbone | |
| 5,376,124 A | 12/1994 | Gustke et al. | |
| 5,470,336 A * | 11/1995 | Ling et al. | 606/105 |
| 5,507,831 A | 4/1996 | Burke | |
| 5,507,832 A | 4/1996 | Michielli et al. | |
| 5,554,192 A | 9/1996 | Crowninshield | |
| 5,569,255 A | 10/1996 | Burke | |
| 5,658,351 A * | 8/1997 | Dudasik et al. | 623/23.48 |
| 5,683,395 A | 11/1997 | Mikhail | |
| 5,693,099 A | 12/1997 | Härle | |
| 5,702,486 A | 12/1997 | Craig et al. | |

(Continued)

FOREIGN PATENT DOCUMENTS

DE  195 18 391 A1  11/1996

(Continued)

*Primary Examiner*—Anuradha Ramana
(74) *Attorney, Agent, or Firm*—Harness, Dickey & Pierce, P.L.C.

(57) ABSTRACT

A jig for positioning an implant at an implantation site in a bone. The jig comprises a first end, a second end opposite the first end, an exterior surface, an interior surface operable to receive at least a portion of the implant, and an engagement surface located at the second end to permit positioning of the jig in the bone. The jig is anchored to the bone to secure the implant in proper position at the implantation site.

12 Claims, 4 Drawing Sheets

U.S. PATENT DOCUMENTS

| | | | |
|---|---|---|---|
| 5,746,771 A | | 5/1998 | Clement, Jr. et al. |
| 5,755,793 A | * | 5/1998 | Smith et al. .............. 623/23.48 |
| 5,766,262 A | | 6/1998 | Mikhail |
| 5,861,043 A | * | 1/1999 | Carn ........................ 623/23.48 |
| 5,885,295 A | | 3/1999 | McDaniel et al. |
| 5,885,299 A | | 3/1999 | Winslow et al. |
| 5,910,172 A | | 6/1999 | Penenberg |
| 5,925,077 A | * | 7/1999 | Williamson et al. ...... 623/22.34 |
| 5,951,561 A | * | 9/1999 | Pepper et al. .................. 606/80 |
| 5,984,968 A | * | 11/1999 | Park ........................ 623/16.11 |
| 5,997,581 A | * | 12/1999 | Khalili .................... 623/23.48 |
| 6,110,175 A | | 8/2000 | Scholl |
| 6,126,691 A | | 10/2000 | Kasra et al. |
| 6,168,627 B1 | | 1/2001 | Huebner |
| 6,168,628 B1 | | 1/2001 | Huebner |
| 6,174,335 B1 | | 1/2001 | Varieur et al. |
| 6,193,758 B1 | | 2/2001 | Huebner |
| 6,251,141 B1 | | 6/2001 | Pierson, III et al. |
| 6,267,785 B1 | | 7/2001 | Masini |
| 6,277,123 B1 | | 8/2001 | Maroney et al. |
| 6,379,391 B1 | | 4/2002 | Masini |
| 6,395,004 B1 | | 5/2002 | Dye et al. |
| 6,494,913 B1 | | 12/2002 | Huebner |
| 6,500,209 B1 | | 12/2002 | Kolb |
| 6,517,581 B2 | * | 2/2003 | Blamey ................... 623/22.12 |
| 6,652,589 B2 | | 11/2003 | Schmotzer et al. |
| 6,669,734 B2 | | 12/2003 | Spotorno et al. |
| 7,044,978 B2 | | 5/2006 | Howie et al. |
| 7,179,264 B2 | * | 2/2007 | Cassell ........................ 606/92 |
| 2002/0045948 A1 | | 4/2002 | Schmotzer et al. |
| 2002/0095217 A1 | | 7/2002 | Masini |
| 2003/0149486 A1 | | 8/2003 | Huebner |
| 2003/0171816 A1 | | 9/2003 | Scifert et al. |
| 2004/0122437 A1 | | 6/2004 | Dwyer et al. |

FOREIGN PATENT DOCUMENTS

| | | |
|---|---|---|
| EP | 0 743 048 A2 | 11/1996 |
| EP | 1 082 943 A2 | 3/2001 |
| FR | 2 595 565 | 9/1987 |
| FR | 2 686 016 | 7/1993 |
| JP | 2-277452 | 11/1990 |
| JP | 5-123333 | 5/1993 |
| WO | WO 93/01769 | 2/1993 |
| WO | WO 93/02641 | 2/1993 |

* cited by examiner

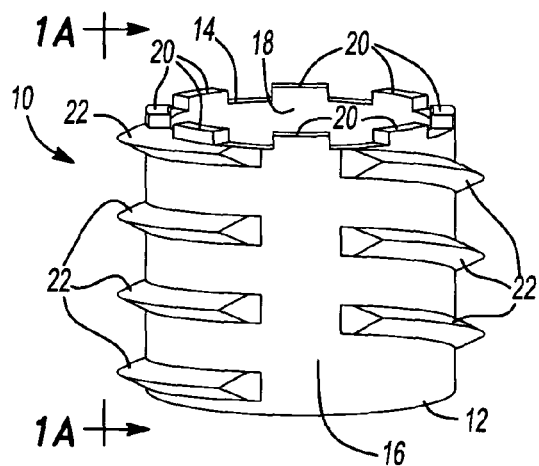
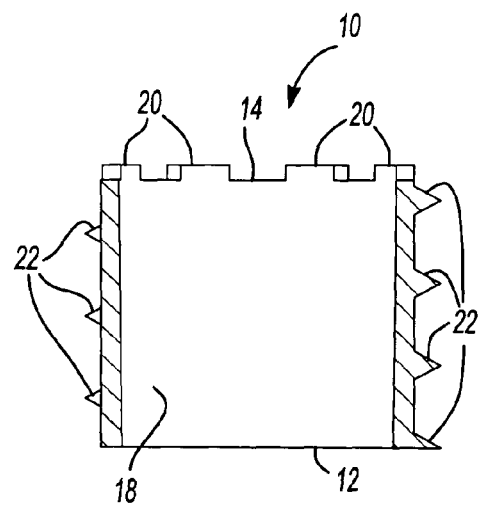
Fig-1
Fig-1A
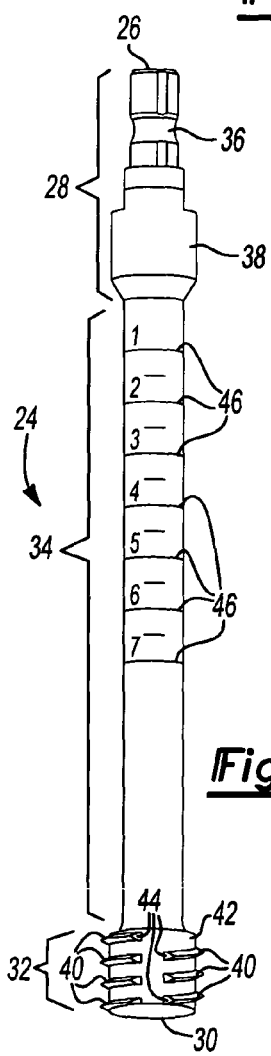
Fig-2
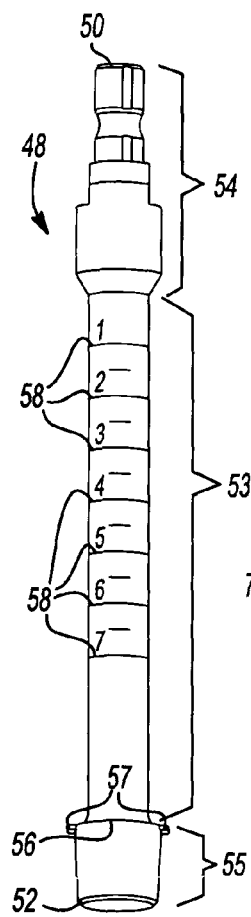
Fig-3
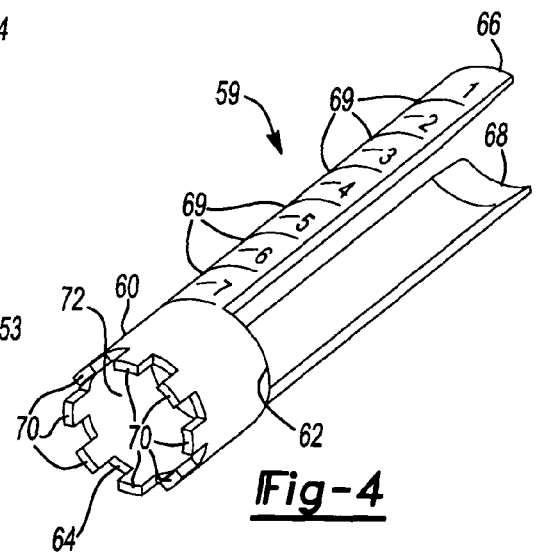
Fig-4

METHOD AND APPARATUS FOR POSITIONING AN IMPLANT

FIELD OF THE INVENTION

The present invention generally relates to prosthetic implant positioning devices. In particular, the present invention relates to a positioning jig for properly positioning an implant during shoulder arthroplasty for fractures of the proximal humerus.

BACKGROUND OF THE INVENTION

Fractures of the proximal humerus may occur due to injury or weakened bone. Often, the proximal humerus fractures at different points into multiple fragments, such as the greater tuberosity, the lesser tuberosity, the head, and the shaft. Such fractures may require the replacement of the proximal humerus with an implant. The implant generally consists of a head, neck, and stem.

To insure that the implant is properly positioned at the proximal humerus, a positioning jig may be used. Conventional positioning jigs typically engage either an exterior or interior portion of the remaining humerus as well as the trial implant and/or the permanent implant. Such positioning jigs permit joint reduction with the trial as well as use of the jig to position the permanent implant in substantially the same position as the trial.

While current fracture jigs are suitable for their intended uses, they are all subject to improvement. The present invention provides a simplified, easy to use, and efficient fracture jig device, system, and method for positioning both a trial implant and a permanent implant at an injury site.

SUMMARY OF THE INVENTION

In one embodiment the present invention provides for a jig for positioning an implant at an implantation site in a bone. The jig comprises a first end, a second end opposite the first end, an exterior surface, an interior surface operable to receive at least a portion of the implant, and an engagement surface operable to permit positioning of the jig in the bone. The jig is positioned within the bone to secure the implant in proper position at the implantation site.

In another embodiment, the present invention provides for a fracture jig positioning system for use at an implantation site. The system is generally comprised of a jig, an insertion tool, and an implant. The jig has a first end, a second end opposite the first end, a cavity operable to receive an implant, and an engagement detail at the second end. The insertion tool has a head operable to mate with the jig and an engagement surface operable to mate with the engagement detail. The jig is implanted at the implantation site using the insertion tool at a position to properly support the implant at the implantation site.

In yet another embodiment, the present invention provides for a method for using a fracture jig to position an implant at an implantation site. The method comprises the steps of preparing the implantation site, positioning the fracture jig at the implantation site, supporting the implant at the implantation site using the fracture jig so that the implant may not directly contact an interior surface of a humeral canal of the implantation site the implantation site, and securing the implant at the implantation site using bone cement.

Further areas of applicability of the present invention will become apparent from the detailed description provided hereinafter. It should be understood that the detailed description and specific examples, while indicating the embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a perspective view of a jig illustrated in accordance with an embodiment of the present invention;

FIG. 1a is cross-sectional view of the jig of FIG. 1 taken along line 2-2 of FIG. 1;

FIG. 2 is a perspective view of a tapping device used to prepare the humerus to receive the jig of FIG. 1;

FIG. 3 is a perspective view of an insertion device operable to insert the jig of FIG. 1 within the humerus;

FIG. 4 is a perspective view of an alternative insertion device operable to insert the jig of FIG. 1 within the humerus;

DETAILED DESCRIPTION OF THE PREFERRED EMBODIMENTS

Figure 7:
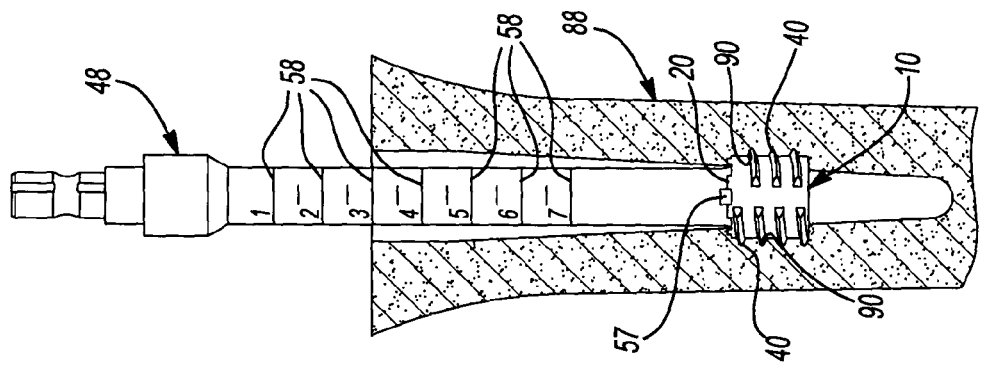
FIG. 7 is a side view of the insertion device of FIG. 3 inserted within the prepared proximal humerus of FIG. 6 to implant the jig of FIG. 1 within the humerus.

The following description of the embodiments is merely exemplary in nature and is in no way intended to limit the invention, its application, or uses. While the invention is described below as a positioning device, system, and method for a humeral implant, the invention may be used to properly position a variety of different bony and non-bony implants in both human and non-human patients. Further, while the invention is described as a fracture jig, the invention may be used to trial and/or retain an implant regardless of whether a fracture has actually occurred.

A jig in accordance with an embodiment of the present invention is illustrated in FIGS. 1 and 1a at 10. As illustrated, the jig 10 generally takes the form of a closed circular sleeve that is a single integral unit. However, the illustration of jig 10 at FIG. 1 is for demonstrative purposes only as the jig 10 may be an open circular or non-circular sleeve comprised of a single unit or multiple parts. The jig 10 generally includes a first end 12, a second end 14, an exterior surface 16, and an interior surface 18.

The second end 14 of the jig 10 includes at least one detail 20. As illustrated, the detail 20 is a projection that extends from the second end 14. However, the detail 20 may be a recess within the second end 14 or may be any other suitable engagement surface to permit engagement between the jig 10 and a suitable implantation tool, discussed in detail below. For example, detail 20 does not need to be located at the second end 14 and may be a projection located on the interior surface 18 that engages flutes on the stem of an implant and/or insertion tool.

The exterior surface 16 optionally includes at least one extension or rib 22. The ribs 22 project from the exterior surface 16 and extend in a circular, stepwise fashion or in any other manner about the exterior surface 16. The ribs 22 may be of various shapes and sizes, but are configured for receipt by corresponding depressions at an implantation site. Any other type of retention feature to retain the jig 10 may also be used, such as threads or an annular feature. As illustrated, the ribs 22 do not extend continuously about the exterior surface 16. However, FIGS. 1 and 1a are for demonstrative purposes only and the ribs 22 may extend about the exterior surface 16 in either a continuous or non-continuous configuration. The ribs 22 may be angled to decrease the force required to implant the jig 10 and/or make the jig 10 self-tapping. In addition to, or in place of, providing angled ribs 22, the first end 12 and/or the exterior surface 16 may optionally include various other features to make the jig 10 self-tapping.

With particular reference to FIG. 1a, the interior 18 of the jig 10 is open at both the first end 12 and the second end 14 to receive and hold any suitable implant. Alternatively, the jig 10 may be opened at one end to receive the distal most portion of the implant. To better secure the implant within the interior 18, the interior 18 may be tapered from the second end 14 to the first end 12 with the second end 14 having a greater diameter than the diameter of the first end 12. The taper of the interior 18 may substantially match the taper of the stem of a typical implant inserted within the interior 18. Alternatively, any other type of suitable engagement surface may also be employed. For example, interior 18 may include an internal feature that acts as a stop or locating device for receiving an implant.

The overall size of the jig 10 may vary depending upon the dimensions of the site that it is to be implanted at. Further, the jig 10 may be available in various different lengths and widths. Still further, the diameter of the interior 18 of the jig 10 may also vary, depending upon both the dimensions of the implantation site and the dimensions of the implant to be received by the interior 18. The diameter of the interior 18 may vary together with, or apart from, changes in the overall size of the jig 10.

The jig 10 may be made from a variety of suitable materials. It is preferred that the jig 10 be made from polymethyl-methacrylate. However, any suitable plastic, bone cement, resorbable material, or biocompatible non-resorbable material may be used.

FIG. 2 illustrates a tapping device at 24. The tapping device 24 generally comprises a first end 26 having a shank 28, a second end 30 having a cutting implement 32, and an elongated shaft 34 that connects the first end 26 to the second end 30.

The shank 28 is any typical shank operable to permit control of the tapping device 24 by a suitable instrument, such as a T-handle (not shown). As illustrated, the shank 28 has a recessed control surface 36 for cooperation with, for example, the T-handle and a collar 38 that acts as a stop to prevent the tapping device 24 from drilling to far within the implantation site. The shape and configuration of the shank 28 may vary to permit cooperation with different control instruments, in addition to, or instead of, the T-handle.

The cutting implement 32 comprises a series of ribs 40 that extend from an outer surface 42. The ribs 40 extend about the implement 32 in a stepped, spiral orientation. As illustrated, the ribs 40 do not extend around the outer surface 42 in a continuous manner, but are instead interrupted at the same interval in each rib 40. However, it must be noted that in particular applications the ribs 40 may be configured to extend continuously about the implement 32. The ribs 40 include leading edges 44 that may be angled to assist in cutting and chipping bone of the implantation area to create threads at the implantation area. It must be noted that this description of the ribs 40 is merely exemplary as the ribs 40 may be of a variety of different design configurations.

The elongated shaft 34 optionally includes a series of score marks 46. The score marks 46 are positioned at regular intervals along the shaft 34. The score marks 46 may include a series of dashes, numbers, letters, or any combination thereof. The score marks 46 may extend the length of the shaft 34 or only a portion of the shaft 34.

With reference to FIG. 3, an inserter for implanting the jig 10 is illustrated at 48. The inserter 48 generally comprises a first end 50, a second end 52 opposite the first end 50, and an intermediary portion 53 that connects the first end 50 to the second end 52. The first end 50 has a shank 54 that is substantially similar to the shank 28 of the tapping device 24. The description of the shank 28 above also applies to the shank 54, thus making it unnecessary to include a description of the shank 54 here.

The second end 52 comprises a head 55 defined, in part, by the second end 52 and an upper head region 56. The head 55 may be of different sizes depending on the size of the jig 10. The second end 52 is tapered inward, toward an interior of the inserter 48, at its terminus. The upper head region 56 includes at least one engagement surface 57. The engagement surface 57 may be an extension as illustrated or may be a recess located within the upper head region 56.

The intermediary portion 53 is longer, by approximately 10 mm, than the elongated shaft 34. The intermediary portion 53 may include a series of score marks 58. The score marks 58 may be any suitable reference markings, such as numbers or letters. The score marks 58 are positioned at intervals that are at least substantially equal to the score marks 46 of the tapping device 24. The score marks 58 may extend from the shank 54 to a distance down the intermediary portion 53 substantially equal to a distance that the score marks 46 extend from shank 28.

FIG. 4 illustrates an inserter 59 according to a second embodiment. The inserter 59 generally comprises a main body 60, a first end 62, and a second end 64 opposite the first end 62. Extending from the first end 62 is a first handle 66 and a second handle 68. Both the first handle 66 and the second handle 68 include score marks 69 that are substantially the same as the score marks 58 of inserter 48. The second end 64 includes a jig engagement detail 70. The jig engagement detail 70 may be a tab that extends from the second end 64 as illustrated, or may be a recess within the second end 64. Extending through the main body 60 is an inner region 72. Generally, the diameter of the inner region 72 is tapered from the first end 62 to the second end 64 and is at least as large as the interior 18 of the jig 10. The inserter 59 may be of various different sizes depending on the size of the jig 10.

Figure 5:
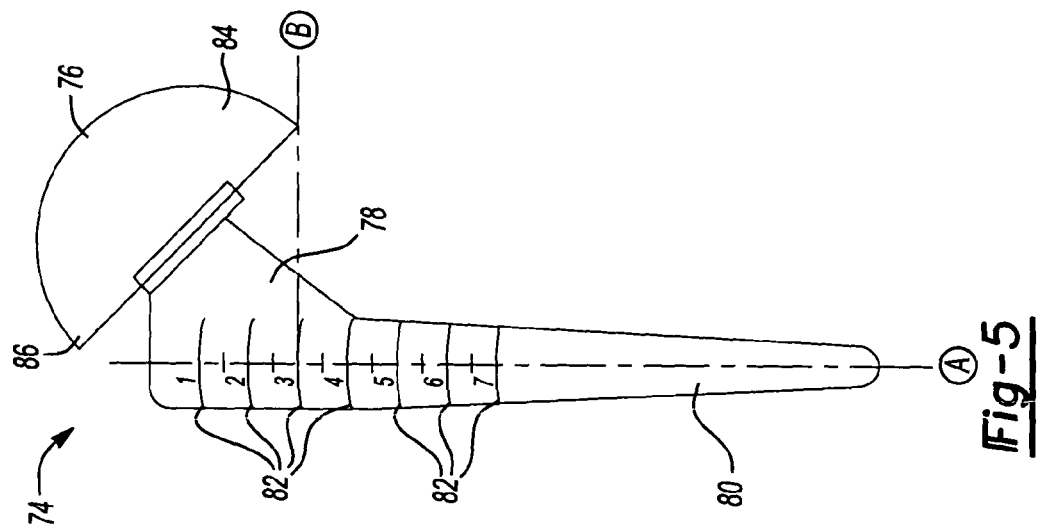
FIG. 5 is a side view of a trial humeral implant.

FIG. 5 illustrates a trial implant at 74. While the trial implant 74 is illustrated as a trial humeral implant, the trial implant 74 may be any suitable bony or non-bony implant. The trial humeral 74 is generally comprised of a head 76, a neck 78, and a stem 80. The stem 80 includes a series of score marks 82. The score marks 82 are Generally positioned at uniform intervals along the stem 80 and are typically either letters or numbers. The trial humeral 74 has a vertical reference line A that extends through the stem 80 and at least a portion of the neck 78. A horizontal reference line B extends from a inferior portion 84 of the head 76, which is at an opposite end of the head 76 from a superior portion 86, to one of the score marks 82.

The trial humeral 74 may be of various different shapes and sizes depending upon the dimensions of the implantation site. In particular, the head 76 may be of different dimensions, with the particular score mark 82 being referenced by the intersection of reference lines A and B being different depending on the size of the head 76. For example, if the head 76 is larger than illustrated, the inferior portion 84 will extend further along the stem 80, thus causing the horizontal reference line B to reference a score mark 82 that is further down the stem 80.

With additional reference to FIGS. 6 through 9 and continued reference to FIGS. 1 through 5, the implantation and operation of the jig 10 will now be described in detail. The description details the implantation of the jig 10 within a fractured humerus 88 to position both the trial humeral implant 74 and a permanent humeral implant that replaces a proximal portion of the humerus 88, including the humeral neck and head (not shown). However, the jig 10 may be implanted in any suitable bony or non-bony surface to position a variety of different implants.

Before the jig 10 is implanted within the fractured humerus 88, the fractured humerus 88 is analyzed by a physician, using conventional techniques, to determine what size trial 74, and specifically what size trial head 76, is required. Once the proper size is determined, the trial head 76 is secured to the neck 78 and the position of the inferior portion 84 of the head 76 is referenced upon the score marks 82 using the point where horizontal reference line B intersects vertical reference line A. The point where reference lines A and B intersect is carefully noted for further use during the implantation process. The size of the trial 74 chosen also has a bearing on the size of the jig 10 used to support the trial 74 and the permanent implant.

Figure 6:
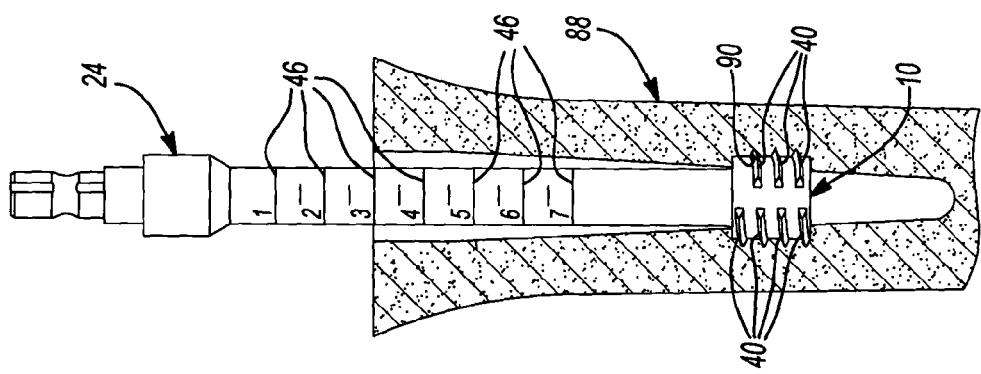
FIG. 6 is a side view of the tapping device of FIG. 1 inserted within a proximal humerus to prepare the humerus for receipt of the jig of FIG. 1.

If the jig 10 is not a self tapping jig, the fractured humerus 88 may be tapped to receive the jig 10. With reference to FIG. 6, to tap the humerus 88, the tapping device 24 is driven within the intact portion of the fractured humerus 88. The tapping device 24 is rotated as it is driven so that the ribs 40 create corresponding grooves 90 within the humerus 88. If the fracture occurs at the medial/inferior intersection of the humeral head and shaft, the tapping device 24 is driven within the humerus 88 until the particular score mark 46 referenced by the intersection of lines A and B on the trial humeral implant 74 is at the surface of the fractured humerus 88, as illustrated in FIG. 6. However, if the fracture is distal to the intersection of the head and shaft, the jig 10 is driven less deeply within the humerus 88.

The score marks 46 on the tapping device 24 and the score marks 82 on the trial implant 74 are calibrated such that when the tapping device 24 is driven within the humerus 88 to a depth such that the score mark 46 corresponding to the score mark 82 at the intersection of reference lines A and B of the trial humeral 74 is at the surface of the fractured humerus 88. The depth of the grooves 90 created by the tapping device 24 are at approximately the proper depth of the jig 10 required to support the trial humeral implant 74, and a permanent humeral implant, in the proper position. However, since the tapping device 24 is generally longer than the inserter 48, the grooves 90 will be of an added depth so that the jig 10 may be driven deeper if necessary.

With reference to FIG. 7, after the humerus 88 is tapped, the inserter 48 is used to implant the jig 10 within the humerus 88. The jig 10 mates with the inserter 48 through cooperation between the engagement surfaces 57 and surfaces between details 20 of the jig 10 when the head 55 is seated within the interior 18 of the jig 10. The inserter 48 is driven within the tapped humerus 88 to a depth such that the score mark 58 of the inserter 48, which is equivalent to the score mark 82 of the trial 74 referenced by the intersection of reference lines A and B, is positioned at the surface of the humerus 88. Driving the inserter 48 to this depth places the jig 10 within the grooves 90 and at an approximate depth to support the trial humeral implant 74 at the correct height.

Alternatively, the inserter 59 may be used to insert the jig 10 within the humerus 88. The inserter 59 engages the jig 10 through cooperation between the sleeve engagement detail 70 and surfaces between details 20 of the jig 10. Using the handles 66 and 68, the jig 10 is driven within the humerus until the score mark 69 corresponding to the score mark 82 referenced on the trial 74 is positioned at the surface of the humerus 88. This is done by placing the inserter 59 over the stem 80 of the trial 74 or the stem of a permanent implant 92 (FIG. 9).

Figures 8, 9:
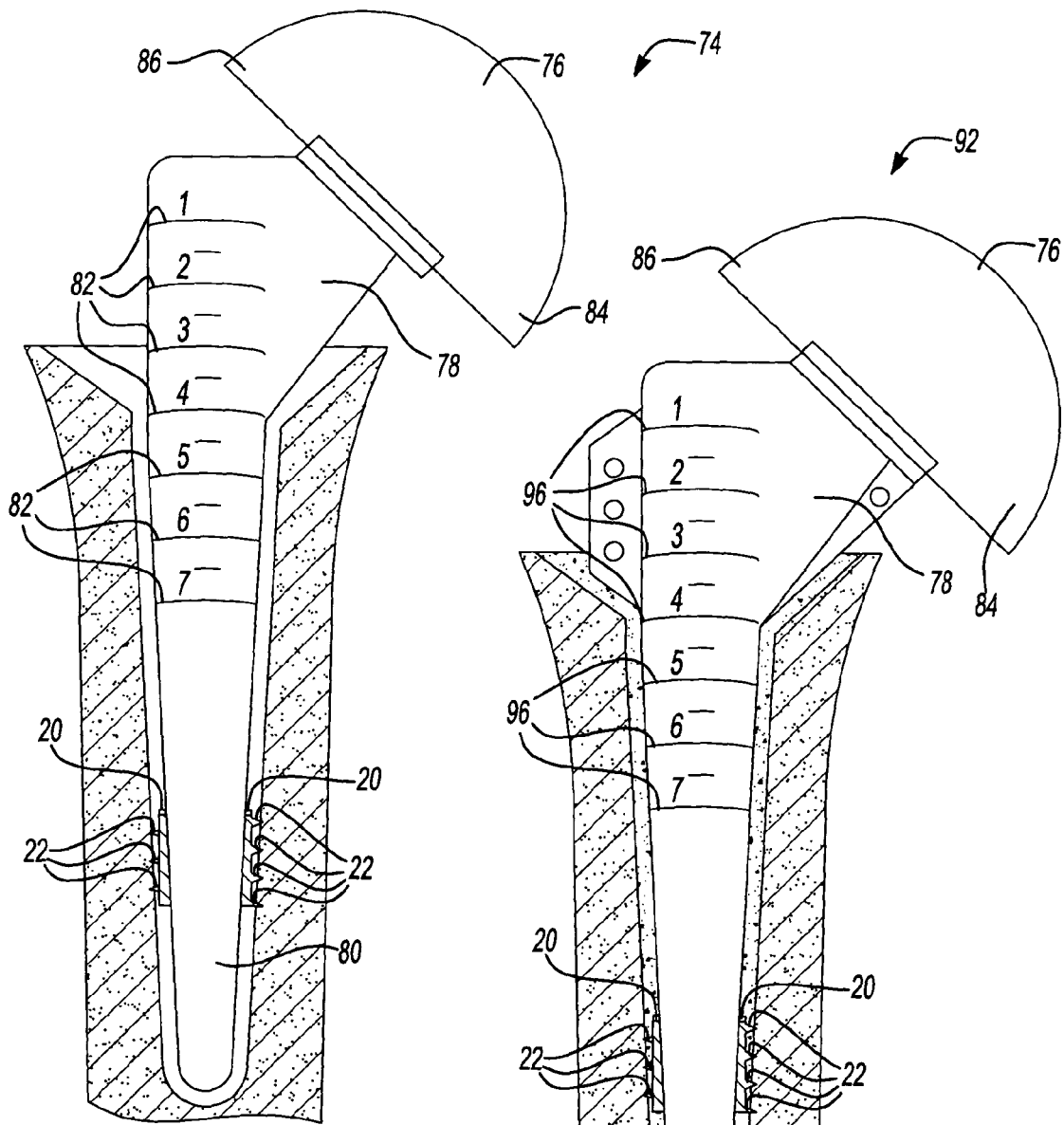
FIG. 8 is a side cross-sectional view of the jig of FIG. 1 seated within the humerus, the jig holding a trial proximal humeral implant within the humerus to permit reduction of the trial joint.
FIG. 9 is a side cross-sectional view of the jig of FIG. 1 seated within the humerus, the jig holding a permanent proximal humeral implant in at least substantially the same position as the trial implant of FIG. 8.

With reference to FIG. 8, after the jig 10 is implanted the trial humeral replacement implant 74 is placed within the humerus 88 such that the stem 80 is seated within the interior 18 of the jig 10. Specifically, the tapered stem 80 is inserted within the tapered interior 18 of the jig 10 until the diameter of the stem 80 becomes the same as or larger than the interior 18 of the jig 10, thus preventing the implant 74 from being inserted further within the jig 10 and humerus 88. The jig 10 supports the trial implant 74 within the humerus 88 to create a substantially even cavity between the trial humeral 74 and the humerus 88 to receive bone cement once the permanent implant 92 is in position.

With the trial humeral 74 supported within the humerus 88 by the jig 10, the humeral joint is reduced. If the trial humeral 74 is not at the correct height, the inserter 48 may be used to adjust the jig 10 accordingly. If the inserter 59 is used, the inserter 59 may remain secured to the jig 10 during the reduction processes because the trial humeral 74 may be inserted through the inner region 72 of the inserter 59. The jig 10 may then be adjusted using the inserter 59 without removing the trial 74.

With reference to FIG. 9, after the trial humeral 74 is properly positioned, it is replaced with the permanent implant 92. Because the dimensions of the permanent implant 92 are substantially similar to the dimensions of the trial humeral 74, when the permanent implant 92 is seated within the interior 18 of the jig 10, it will be in substantially the same position as the trial humeral 74 was. Because the permanent implant 92 is substantially similar to the trial humeral 74, the permanent implant 92 need not be described in detail. As with the trial implant 74, support of the permanent implant 92 within the humerus 88 forms a substantially even cement mantle between the permanent implant 92 and the humerus 88 and prevents the permanent implant 92 from contacting the humerus 88. Before the permanent implant 92 is supported by the jig 10 in proper position, bone cement 94 is introduced within the humerus 88 and later hardens within the mantle formed between the implant 92 and the humerus 88 to affix the implant 92 within the humerus. The permanent implant 92 may be provided with reference marks 96, which are similar to the marks 82 of the trial 74, to insure that the permanent implant 92 is in relatively the same position as the trial 74.

Figure 10:
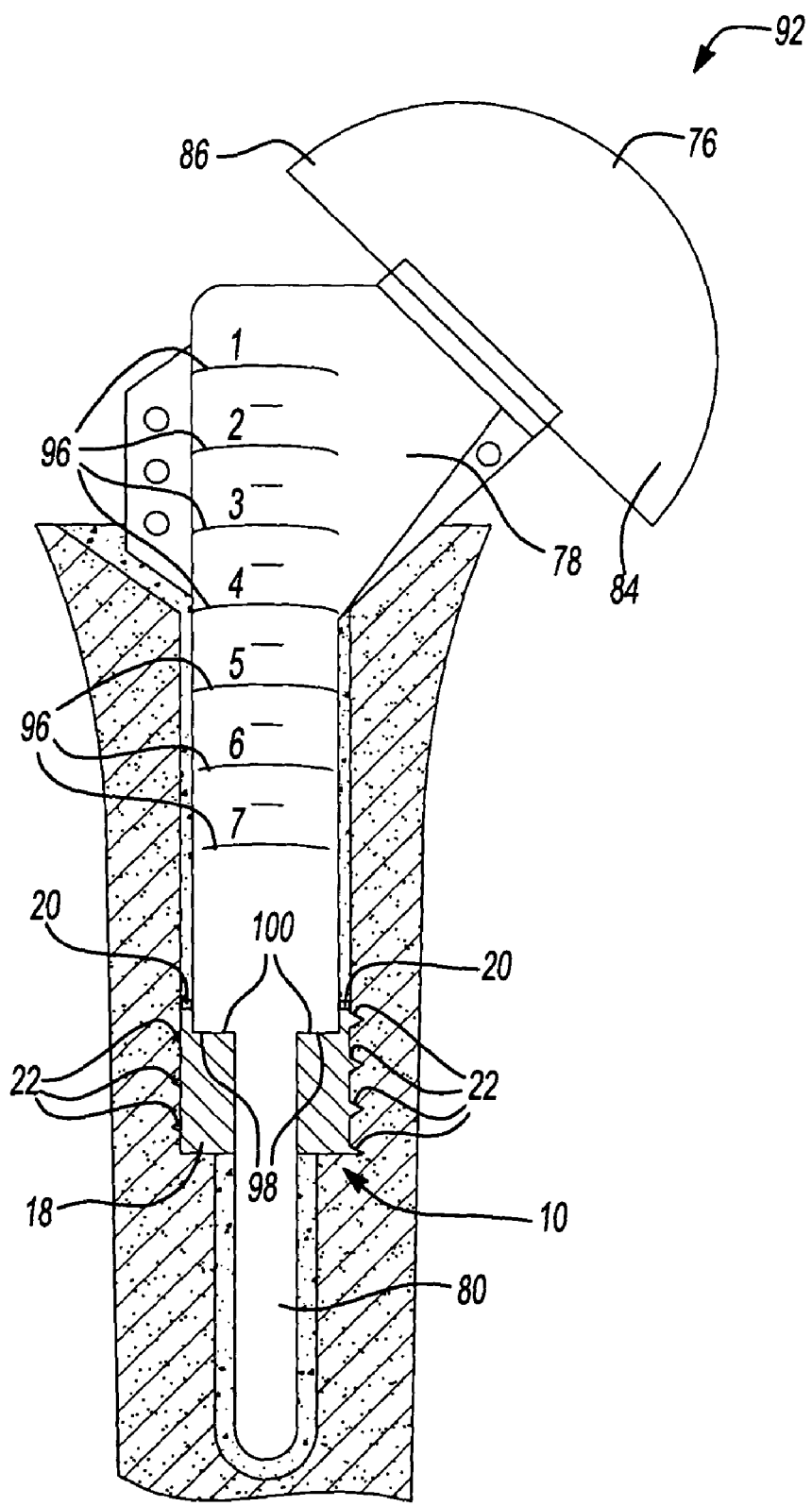
FIG. 10 is a side cross-sectional view of a jig illustrated in accordance with an alternate embodiment of the present invention, the jig seated within the humerus and holding a permanent proximal humeral implant.

The above description is meant to encompass various additional embodiments of the present invention. For example, with reference to FIG. 10, the interior 18 of the implant 10 may have parallel sidewalls. Further the implant 10 may have a receiving surface 98 operable to receive the trial implant 74 and the permanent implant 92, as illustrated. The receiving surface 98 may be any suitable surface or detail operable to mate with a corresponding stop surface or detail, such as stop surface 100, of the trial implant 74 or the permanent implant 92, as illustrated. In the exemplary embodiment of FIG. 10, the receiving surface 98 is a recessed surface of the interior 18 proximate to the second end 14 and the stop surface 100 is a stepped surface of the stem 80.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A fracture jig positioning system for use at an implantation site comprising:
   a jig having:
      a first end;
      a second end opposite said first end; and
      a cavity having an inner surface that is at least substantially smooth and operable to axially receive an implant and secure the implant in at least a substantially non-rotational manner;
   an insertion tool having
      a head operable to mate with said jig, said insertion tool having a series of reference marks; and a tapping device for preparing said implantation site having:
   a shank having a control surface operable to engage a control device;
   a cutting implement having a cutting surface; and
   an elongated shaft connecting said cutting implement to said shank, said elongated shaft having a series of tick marks;
   wherein said implant includes a series of score marks;
   wherein said jig is implanted at the implantation site using said insertion tool at a position to properly support said implant at the implantation site; and wherein said series of tick marks of said elongated shaft are substantially the same as said score marks of said implant and said reference marks of said insertion tool.

2. The fracture jig positioning system of claim 1, wherein said insertion tool further comprises a shank operable to engage a control device.

3. The fracture jig positioning system of claim 1, wherein said insertion tool further comprises a first handle and a second handle.

4. The fracture jig positioning system of claim 1, wherein said jig is self-tapping.

5. The fracture jig positioning system of claim 1, wherein said jig is resorbable.

6. The fracture jig positioning system of claim 1, wherein said inner surface of said jig is tapered from said second end to said first end such that said inner surface has a diameter at said second end that is greater than a diameter at said first end.

7. The fracture jig positioning system of claim 6, wherein said head of said tool is operable to mate with said interior cavity of said jig to implant said jig at the implantation site.

8. The fracture jig positioning system of claim 1, wherein said implant is a trial implant.

9. The fracture jig positioning system of claim 1, wherein said implant is a permanent implant.

10. The fracture jig positioning system of claim 1, wherein said jig further comprises:
    a retention feature extending from an exterior surface of said jig.

11. The fracture jig positioning system of claim 1, said jig further having a receiving surface operable to mate with said implant.

12. The jig of claim 1, wherein said head is operable to mate with said inner surface of said jig to form a taper lock between said head and said inner surface.

* * * * *